(12) United States Patent  
Esser

(10) Patent No.: US 8,381,572 B2
(45) Date of Patent: Feb. 26, 2013

(54) DEVICE FOR RECORDING MEASUREMENT DATA

(75) Inventor: Daniel Esser, Hamburg (DE)

(73) Assignee: Contros Systems & Solutions GmbH, Kiel (DE)

( * ) Notice: Subject to any disclaimer, the term of this patent is extended or adjusted under 35 U.S.C. 154(b) by 301 days.

(21) Appl. No.: 12/309,390

(22) PCT Filed: Jul. 27, 2007

(86) PCT No.: PCT/DE2007/001373
§ 371 (c)(1),
(2), (4) Date: Jan. 14, 2009

(87) PCT Pub. No.: WO2008/011881
PCT Pub. Date: Jan. 31, 2008

(65) Prior Publication Data
US 2009/0241637 A1 Oct. 1, 2009

(30) Foreign Application Priority Data

Jul. 28, 2006 (DE) .......................... 10 2006 035 788

(51) Int. Cl.
G01N 33/18 (2006.01)
(52) U.S. Cl. ........................................ 73/19.1
(58) Field of Classification Search ................ 73/19.1
See application file for complete search history.

(56) References Cited

U.S. PATENT DOCUMENTS

| 7,059,206 | B1 * | 6/2006 | Kingston et al. ............ 73/863.23 |
| 2005/0160801 | A1 * | 7/2005 | Brumboiu et al. ............ 73/64.56 |
| 2005/0241382 | A1 * | 11/2005 | Coenen ........................ 73/152.19 |

FOREIGN PATENT DOCUMENTS

| DE | 40 07 375 | 10/1990 |
| DE | 40 40 329 | 8/1992 |
| DE | 197 08 770 | 8/1998 |
| DE | 198 04 638 | 5/2001 |
| DE | 199 51 163 | 5/2001 |
| DE | 101 33 466 | 1/2003 |
| DE | 102005037529 | 2/2006 |
| DE | 102005020131 | 5/2006 |
| DE | 699 26 845 | 6/2006 |
| EP | 0 869 359 | 10/1998 |
| EP | 0 823 055 | 10/2001 |
| WO | 96/37771 | 11/1996 |

OTHER PUBLICATIONS

Garcia and Masson, "Environmental and geologic application of solid-state methane sensors," Environmental Geology 2004 p. 1059-1063.*

* cited by examiner

Primary Examiner — Hezron E Williams
Assistant Examiner — Gregory J Redmann
(74) Attorney, Agent, or Firm — Lucas & Mercanti, LLP; Klaus P. Stoffel

(57) ABSTRACT

The device is used to record measurement data and has a housing, a housing interior and a membrane that is held by the housing and delimits the housing interior in regions. At least one sensor is arranged inside the housing interior. Furthermore, a thermocatalytic element for the decomposition of at least one gas is arranged in the housing interior.

7 Claims, 2 Drawing Sheets

DEVICE FOR RECORDING MEASUREMENT DATA

BACKGROUND OF THE INVENTION

The invention concerns a device for acquiring measurement data, which has a housing, an inner chamber of the housing, and a membrane that is supported by the housing and bounds part of the inner chamber of the housing, and in which at least one sensor is installed within the inner chamber of the housing.

Devices of this type use measurement technology, for example, to determine gases that pass through the membrane. In this regard, first, the membrane shields the sensor from the environment, and, second, the membrane ensures that only predefined gases are able to enter the area of the sensor in appreciable concentrations. Sensor systems of this type are described, for example, in EP 0 823 055 B1 and EP 1 114 297 B1.

One problem with the use of sensors and measurement systems of this type is that the gases that pass through the membrane to enter the environment of the sensor escape back out of the area of the sensor at only a relatively slow rate when the gas concentration in the vicinity of the measurement system changes. When the gases to be detected are present in concentrations that vary as a function of time, this gives rise to significant time constants, which result in measuring sluggishness of the overall system.

Therefore, in the case of movement through a local measurement area with different concentrations to be measured or with concentrations to be measured that vary as a function of time, the previously known measurement systems are still not able to meet all of the requirements that are placed on optimum measurement quality.

SUMMARY OF THE INVENTION

Therefore, the objective of the present invention is to improve a device of the type described above in such a way that improved measurement dynamics are obtained.

In accordance with the invention, this objective is achieved by installing a thermocatalytic element in the inner chamber of the housing to decompose at least one gaseous hydrocarbon and by designing the inner chamber of the housing in a way that supports gas circulation.

By installing a thermocatalytic element in the inner chamber of the housing, it is possible significantly to minimize interfering gas concentrations within a short period of time. These may be gases that pass through the membrane along with the gas to be measured and would otherwise distort the measurement result. In particular, however, the gas to be measured can be thermocatalytically decomposed to support a highly dynamic measurement with only slight time-lag effects. Especially thermocatalytic sensors, so-called pellistors, can be used as the thermocatalytic elements.

The measurement system of the invention is suitable, for example, for detecting leaks in offshore pipelines. Due to its very rapid response time, it can also be used in submersible vehicles. Since its long-term stability is very high, the measurement system of the invention is also suitable for long-term applications over periods of a year or more. When optical sensors are used, long-term stability of up to ten years is achieved.

Gas circulation can be actively generated by impellers or can be produced as a secondary effect of the thermocatalytic decomposition. The thermocatalytic decomposition usually leads to local gas heating, which causes movement of the gases enclosed in the inner chamber of the housing. Local gas flow or gas turbulence can be generated especially by a suitable design of the walls of the inner chamber of the housing, and this promotes contact of the hydrocarbons that penetrate the inner chamber of the housing through the membrane with the thermocatalytic sensor.

Use of the measurement system of the invention in the petroleum industry is possible if the thermocatalytic element is designed for the decomposition of at least one hydrocarbon.

Offshore applications are made possible by designing the housing for use in water.

Pipeline leak detection is promoted by designing the measurement system for underwater gas detection.

Extremely high measurement accuracy can be realized by designing the sensor as an optical sensor.

To promote low energy consumption, it is proposed that the sensor be designed as a semiconductor sensor.

It is advantageous to design the membrane to be gas-permeable.

Simple realization of the membrane from the standpoint of production engineering is promoted by forming the membrane as a coating.

Arrangement of the membrane on the sensor contributes to a compact design.

High pressure stability can be realized by mounting the membrane on a gas-permeable carrier.

High pressure resistance combined with low flow resistance to the gas to be measured can be achieved by constructing the carrier of a porous material.

Designing the membrane to be gas-permeable in both directions contributes to a high degree of measurement dynamics.

Short response times are promoted by installing a pump on the outside of the housing.

It is conducive to sustained underwater use if the membrane has antifouling properties.

The installation of a temperature stabilizer in the inner chamber of the housing helps to further ensure highly accurate measuring results.

Further reduction of the response times can be achieved by installing at least one pump in the inner chamber of the housing.

Specific embodiments of the invention are schematically illustrated in the drawings.

DETAILED DESCRIPTION OF THE INVENTION

Figure 1:
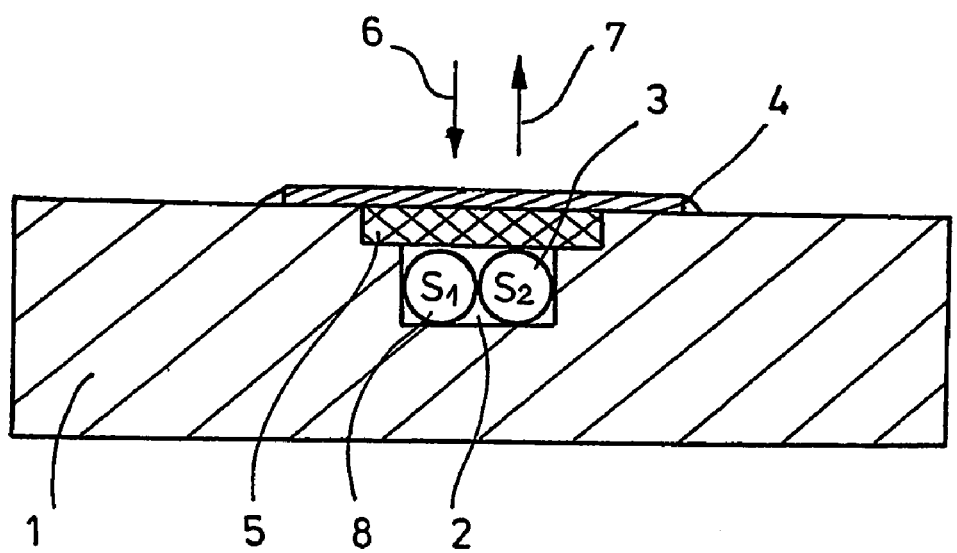
FIG. 1 shows a schematic cross section through a measurement system.

In the embodiment shown in FIG. 1, the measurement system consists of a housing 1, which has an inner chamber 2. A sensor 3 is installed in the inner chamber 2. A membrane 4 bounds part of the inner chamber 2 and is supported by the housing 1. The membrane can be designed as a conventional membrane or can be formed as a coating. In the illustrated embodiment, the membrane extends partly beyond a carrier 5. This provides increased mechanical stability. The carrier 5 can consist of any desired gas-permeable materials. Especially the use of a porous material is contemplated.

The membrane 4 is gas-permeable in both directions, so that gas flow can occur in both an inflow direction 6 and an outflow direction 7.

The sensor 3 can be designed, for example, for the detection of hydrocarbons or other gases. For example, methane, butane, or propane can be measured. However, it is also basically possible to use the sensor 3 to determine any other desired physical, chemical, or biological parameters.

A thermocatalytic element 8 is also installed in the inner chamber 2 next to the sensor 3. The thermocatalytic element 8 can be realized, for example, as a thermocatalytic sensor. A thermocatalytic sensor usually carries out the combustion of a substance that is to be decomposed. For example, it is possible, with the addition of oxygen, to decompose methane thermocatalytically into carbon dioxide and water.

Figure 2:
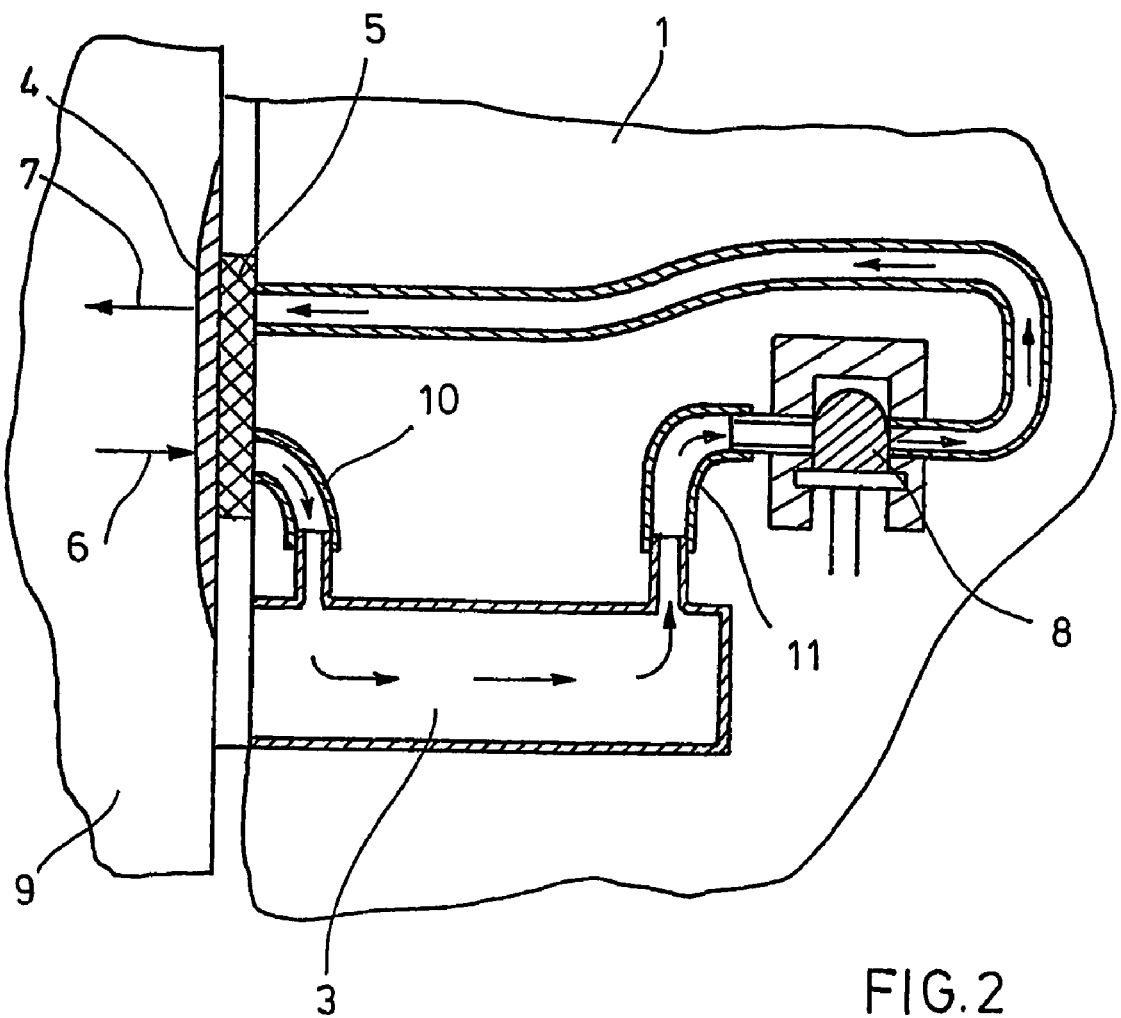
FIG. 2 is a schematic drawing that illustrates the operating principle.

FIG. 2 illustrates one use of the measurement system. In this case, gas circulation is provided within the housing 1, for example, by at least one pump (not shown). Gas passing through the membrane 4 from an external medium 9, for example, water, is conveyed through a line 10 to the sensor 3, through which it flows. The gas is then conveyed past a thermocatalytic element 8 through a line 11 and passes back out through the membrane 4. In this connection, the fraction of gas of measurement interest is reduced with the use of the thermocatalytic element 8 in such a way that the emerging gas does not appreciably adulterate the gas entering in the inflow direction 6 with respect to the concentrations of interest.

Examples of sensors 3 that can be used are optical sensors or semiconductor sensors. Membranes 4 are understood to include both actual membranes and coatings with membrane-like properties.

Silicones or silicone-like substances can be used as materials for making the membrane 4, but in principle it is also possible to use a variety of other materials. The membrane 4 typically has both the function of selectively supplying the gas to be measured to the sensor 3 and the function of protecting the sensor 3 from penetration by water in the case of underwater applications. It is also possible to use variants of membranes that allow all gases contained in the water to pass through. The carrier 5 has been found to be advantageous especially when the measurement system is used at great water depths, since it greatly improves the mechanical stability of the membrane 4. The design allows applications at depths of up to 6,000 meters.

With the use of the measurement system, it is possible to measure both gases dissolved in the water and, for example, gases present in the water in the form of gas bubbles or adsorbed gases. The measurement system can also be inserted in sediment or on the ocean floor for measuring gases present there, for example, hydrocarbons. Besides the aforementioned measurement of hydrocarbons, such as methane, ethane, propane, and butane, other gases, for example, carbon dioxide or hydrogen sulfide, can also be measured by selecting suitable sensors 3.

There are basically many different areas of applications, for example, the following: leakage detection in offshore pipelines, measurements on submarine volcanoes, measurements on hydrothermal vents, measurement in sewage treatment plants of dumps, methane outlets in tunnel shafts for roads, measurement of methane in bore holes, general measurements in oceanography, methane in tidelands, biogas plants, offshore safety on drilling and pumping platforms, production of methane hydrates in the laboratory, exploration of natural gas and petroleum deposits, detection of groundwater emergence near coastlines, methane measurements in oceans and methane gas sources in channels (marine seeps).

Figure 3:
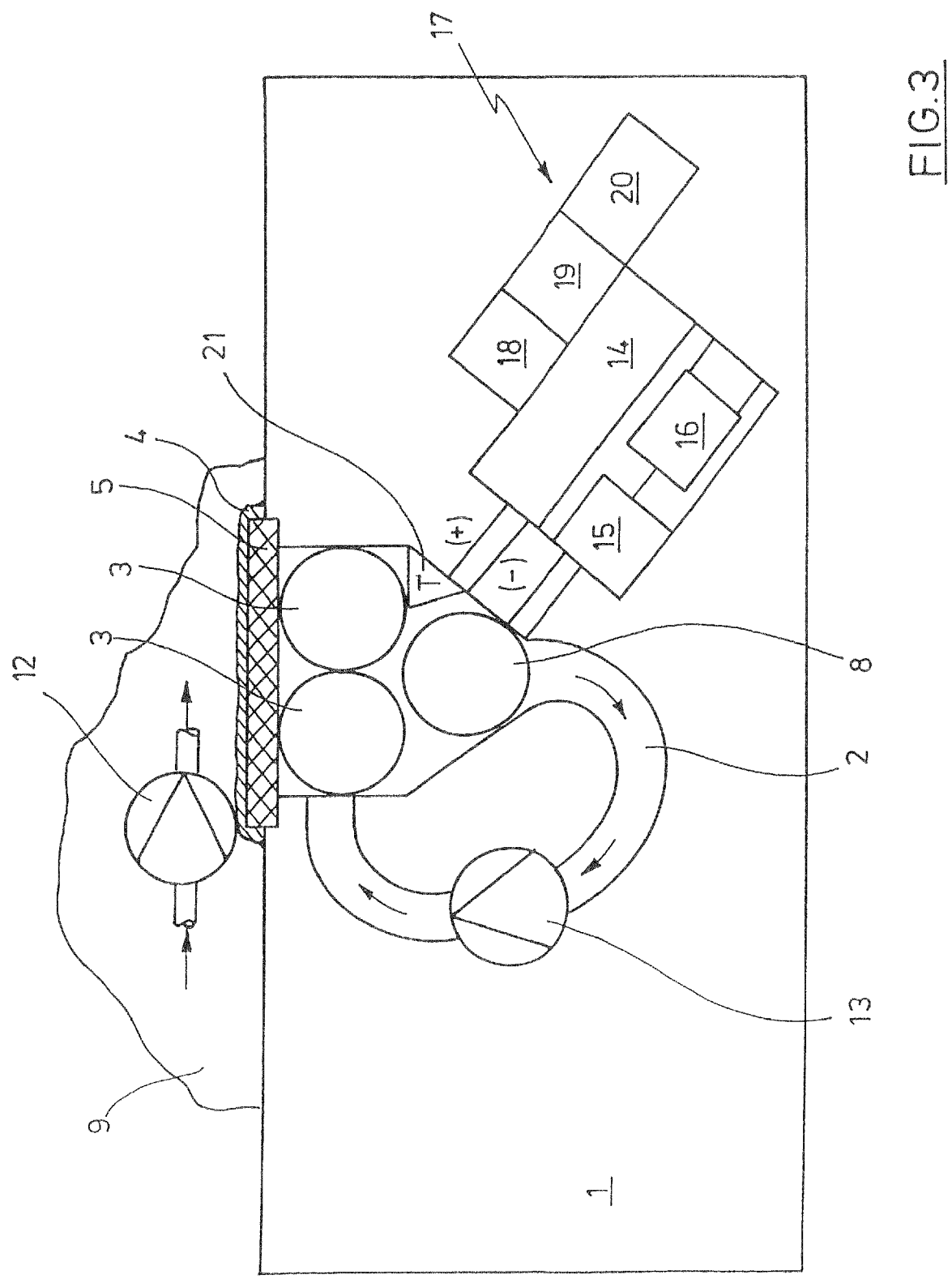
FIG. 3 is a more detailed schematic drawing of the measurement system with the associated electric components.

FIG. 3 shows a more detailed design realization of the measurement system. Two sensors 3 are installed in the inner chamber 2 of the housing. The first sensor 3 is designed as a semiconductor sensor for detecting at least one gas. The second sensor 3 is designed as an infrared sensor, especially in the NDIR wavelength range, for the detection of at least one gas. A thermocatalytic sensor realized as a pellistor is used as the thermocatalytic element 8. This sensor is suitable for the detection of hydrocarbons and, specifically, can carry out a combustion of hydrocarbons.

A pump 12 is installed on the outside of the housing 1. If the external medium 9 is water, the pump 12 is realized as a water pump. The pump 12 produces flow of the water and thus of the gases dissolved in the water in the direction of the membrane 4, thereby causing turbulence in the vicinity of the outer boundary of the membrane 4. This turbulence leads to increased desorption of the gas by the membrane 4. The inner chamber 2 of the housing is equipped with a pump 13 to promote gas circulation and thus further increase measuring effectiveness.

The measurement system has a power supply 14. To allow mobile applications, the power supply 14 is realized, for example, as a battery or secondary cell. In a typical embodiment, the sensor or sensors 3 are realized as analog sensors, whose output signal is supplied to one or more analog-to-digital converters 15, which convert the measuring signals to digital signals that can be further processed. The analog-to-digital converter 15 can be connected, for example, with a data storage device 16 to document the performance of the measurement and/or to allow time-shifted data evaluation.

The measurement system is also equipped with a control unit 17, which has a memory 18, a monitoring unit 19 and an interface 20. The memory 18 can be designed, for example, as a flash ROM. A mini-PC with one or more microprocessors and other electronic components can be used as the monitoring unit 19. The interface 20 serves especially for carrying out a data transmission, optionally, online or offline.

A temperature stabilizer 21 mounted in the inner chamber 2 of the housing 1 contributes to further improvement of measurement quality. In applications involving moist conditions, the temperature stabilizer 21 prevents especially the temperature from falling below the dew point. In addition, however, large temperature variations would have unfavorable effects on measurement accuracy.

The invention claimed is:

1. A device for acquiring measurement data for determining gases in liquid, which has a housing for use in water, an inner chamber of the housing, and a flat membrane that is supported by the housing and bounds part of the inner chamber of the housing, and in which at least one sensor for measuring gases in liquids is installed within the inner chamber of the housing, wherein the sensor includes a thermocatalytic element (8) for decomposing at least one gaseous hydrocarbon in the inner chamber (2) of the housing and where the inner chamber (2) of the housing is designed in a way that supports gas circulation, wherein a temperature stabilizer is arranged in the housing, the sensor being constructed so that decomposition of a hydrocarbon by the thermocatalytic element takes place in the inner chamber with improved measurement dynamics and reduced lag time, wherein the membrane is gas-permeable in both directions and has a backside mounted on a gas-permeable carrier so that the carrier mechanically reinforces the membrane so as to permit use of the membrane at depths of up to 6,000 meters, wherein a pump for generating continuous gas circulation is arranged in the inner chamber of the housing so that the gas circulation of measurement air is continuous between the membrane and the at least one sensor to provide a continuous equilibration of the same measurement air/medium and reduce reaction time.

2. A device in accordance with claim 1, wherein the sensor (3) is designed as an optical sensor.

3. A device in accordance with claim 1, wherein the sensor (3) is designed as a semiconductor sensor.

4. A device in accordance with claim 1, wherein the membrane (4) is formed as a coating.

5. A device in accordance with claim 1, wherein the carrier (5) is made of a porous material.

6. A device in accordance with claim 1, wherein a pump is installed on the outside of the housing (1).

7. A device in accordance with claim 1, wherein the membrane (4) has antifouling properties.

* * * * *

UNITED STATES PATENT AND TRADEMARK OFFICE
CERTIFICATE OF CORRECTION

PATENT NO.        : 8,381,572 B2
APPLICATION NO. : 12/309390
DATED             : February 26, 2013
INVENTOR(S)       : Daniel Esser It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 417 days.

Signed and Sealed this
First Day of September, 2015

Michelle K. Lee
*Director of the United States Patent and Trademark Office*